US012496416B2

(12) United States Patent
Taicher

(10) Patent No.: US 12,496,416 B2
(45) Date of Patent: Dec. 16, 2025

(54) TRACHEAL INTRODUCER SHEATH

(71) Applicant: Christopher Taicher, Beverly Hills, CA (US)

(72) Inventor: Christopher Taicher, Beverly Hills, CA (US)

( * ) Notice: Subject to any disclaimer, the term of this patent is extended or adjusted under 35 U.S.C. 154(b) by 0 days.

(21) Appl. No.: 17/567,715

(22) Filed: Jan. 3, 2022

(65) Prior Publication Data

US 2023/0166066 A1 Jun. 1, 2023

Related U.S. Application Data

(60) Provisional application No. 63/283,455, filed on Nov. 27, 2021.

(51) Int. Cl.
*A61M 16/04* (2006.01)

(52) U.S. Cl.
CPC .... *A61M 16/0418* (2014.02); *A61M 16/0488* (2013.01); *A61M 2205/0216* (2013.01); *A61M 2205/0266* (2013.01); *A61M 2205/582* (2013.01)

(58) Field of Classification Search
CPC .... A61M 16/04–0459; A61M 16/0463; A61M 16/0475–0497; A61M 25/01–0105; A61M 25/0133; A61M 25/0147; A61M 25/0169–0172; A61M 2025/015; A61M 2025/09116; A61B 1/267–2673
See application file for complete search history.

(56) References Cited

U.S. PATENT DOCUMENTS

| | | | | | |
|---|---|---|---|---|---|
| 3,913,568 | A * | 10/1975 | Carpenter | A61B 1/2733 | 600/142 |
| 5,509,408 | A * | 4/1996 | Kurtis | A61M 16/0484 | 128/207.14 |
| 2010/0224186 | A1* | 9/2010 | Uesugi | A61M 16/0459 | 128/207.14 |
| 2010/0307489 | A1* | 12/2010 | Harms | A61M 16/0488 | 128/200.26 |
| 2011/0077466 | A1* | 3/2011 | Rosenthal | A61B 1/00096 | 600/188 |
| 2013/0000649 | A1* | 1/2013 | Hayman | A61M 16/0479 | 128/207.15 |

(Continued)

OTHER PUBLICATIONS

Characteristics of and Important Lessons From the Coronavirus Disease 2019 (COVID-19) Outbreak in China Summary of a Report of 72 314 Cases From the Chinese Center for Disease Control and Prevention.

*Primary Examiner* — Rachel T Sippel
(74) *Attorney, Agent, or Firm* — Fish & Richardson P.C.

(57) ABSTRACT

A tracheal introducer sheath device (TIS) device is disclosed for guiding the insertion of a tracheal introducer. Tracheal introducer sheath device has a hollowed tube of flexible material that provides a sheath channel for a tracheal introducer. Tracheal introducer sheath device has a proximal end and a distal end. Tracheal introducer is guided via the sheath channel from the proximal end in a controller manner to a glottic opening of a person's airway. Sheath channel in the tracheal introducer sheath device is manually moldable to articulate different angles, wherein the different angles supports the movement of the tracheal introducer deeper into a person's airway.

28 Claims, 9 Drawing Sheets

(56) References Cited

U.S. PATENT DOCUMENTS

| | | | | |
|---|---|---|---|---|
| 2015/0258295 | A1* | 9/2015 | Stocking | A61M 25/01 128/200.26 |
| 2017/0203075 | A1* | 7/2017 | Yan | A61M 16/0493 |
| 2021/0213222 | A1* | 7/2021 | Imeson | A61M 16/049 |
| 2023/0108277 | A1* | 4/2023 | Khanolkar | A61B 1/00082 128/200.26 |

* cited by examiner

TRACHEAL INTRODUCER SHEATH

This application claims priority to provisional eFiled Application No. 63/283,455; EFS ID 44374429; Confirmation Number 1883; Title of Invention: Tracheal Introducer Sheath; First Named Inventor: Christopher Taicher, Receipt Date 27 Nov. 2021.

CROSS-REFERENCE TO RELATED APPLICATIONS

Not Applicable

STATEMENT REGARDING FEDERALLY SPONSORED RESEARCHED OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Severe and critical cases of COVID-19 raise clinical concerns for progression to respiratory failure and a need for airway protection with endotracheal intubation. [What is endotracheal intubation? A procedure typically requiring utilization of a laryngoscope blade in one hand to help visualize the vocal cords ("cords") and glottic opening for passage (with the opposite hand) of an endotracheal tube into the tracheal space.]

Since nearly 20% of past COVID-19 cases were considered severe or critical, according to a large 2020 study in the Journal of the American Medical Association, the U.S. healthcare system must be prepared for spikes in COVID-19 incidence and related increases in frequency of airway failures. The pediatric COVID-19 population characteristics underscore this point: Among 20,714 hospitalized children and adolescents diagnosed with COVID-19, 31% experienced severe COVID-19.

There is an additional problem that proceduralists (emergency medicine physician, anesthesiologist, ambulance personnel, etc.) face: the so-called "difficult airway", or those that pose technical challenges.

Difficult airways represent up to nearly one-quarter of all intubations and according to the American Journal of Respiratory and Critical Care Medicine, are due mostly to a difficulty placing the endotracheal tube. This can be for many reasons including difficulty visualizing the cords due to edema (a well described complication with COVID-19-associated acute respiratory distress syndrome, or ARDS), foreign body, a malignant mass, or simply patient's baseline anatomy. The outcomes of COVID-19-associated ARDS patients are especially grim, with a mortality of 45%, and thus this population deserves special attention in the U.S. research and development spaces.

Regardless of the cause, complicated intubation procedures that take excessive time (with multiple "passes" or attempts at passing an endotracheal tube) are associated with diminished central nervous system oxygenation and potential neurologic disease.

As such, much effort has been put towards improving likelihood of first attempt ("first pass") success during expectedly and unexpectedly difficult intubations. The most notable of airway adjuncts for this purpose is the Bougie Device, patented in 2007 (U.S. Pat. No. US20100307489A1).

Introducers, like the Bougie Device, tend to be helpful because of their relatively small size and (depending on device) kinked and malleable distal tip as compared to an endotracheal tube. Once an introducer is passed through the cords, sometimes blindly (again, due to severe pathology such as edema, or anatomy, or both), tracheal positioning of an introducer is confirmed by feeling tracheal rings as vibratory feedback in the hand operating the introducer. Subsequently, an endotracheal tube is passed over the introducer, and the introducer removed from the patient, for endotracheal tube securing and then attachment to a mechanical ventilator.

Given strong evidence on first-attempt intubation success being significantly higher when using an introducer, intubation proceduralists will likely be continuing to utilize introducers.

The most notable problem with existing introducers, including the Bougie Device, is its limited ability to maintain desired contour and, once they have been placed beyond the oral cavity and oropharynx, take a sharp angle around an often obstructing epiglottis to move through the cords. A kinked or angled introducer tip is extremely limited in taking steep angles because it is pushed by the proceduralist with a force vector driven mostly external to the patient. Sometimes the proceduralist is controlling the introducer within the patient's oropharynx, but this still is relatively external and angled away from the deeper glottic opening. Thus, curving the tip of an introducer that is deep in the patient's airway confers only so much ability to take a steep angle. However limited, an operator can also move the introducer along a curved plane to add some improved angular control.

With both the TIS and STIS, and relatively tiff sheath through which an introducer can move allows the introducer to move along the axis created by the sheath itself, which can be molded quickly to the desired angle, regardless of steepness, up to ninety degrees.

As mentioned, manually molding a kink of varied angles at the tip of an introducer prior to introduction into the patient is common practice to aid its navigation towards and through the cords, however this corrective action has limited utility, including an inability to manipulate the angle once placed into the patient.

The TIS solves this problem by taking on varied angles (articulating between 10 and 90 degrees), in real time, controlled at the proximal end of the TIS (outside of the patient), whilst the distal introducer is placed deeper in the airway.

While a patent pending articulating device (Total Control Introducer by Through The Cords LLC) includes an articulating mechanism, the device is itself an introducer. Uniquely, the TIS is a sheath through which a broad range of introducers can be controlled. As such, varied introducer size, material, shape and design (ie ones with a central lumen for oxygenation or blunt-closed-end tips) can be chosen on a clinical case-by-case basis for utilization with a TIS. For example, a patient with an especially friable airway can be intubated using a TIS and an especially soft tipped introducer to avoid potentially injuring the soft tissue and causing acute and chronic complications, such as bleeding and fistula creation, respectively. Any number of introducer types can be designed and manufactured for assembly with a TIS.

In addition to a TIS allowing for selection of varied introducer types on a clinical case-by-case basis, it eliminates waste of existing supplies of introducers, and supports continued, specialized and streamlined manufacturing.

Another issue with known introducers, Bougie, Frova and others, are their relative unwieldy form. Given they are composed most commonly of thin (commonly approaching 6 mm), lengthy (often between 50 and 70 centimeters), PTFE, they produce a somewhat flimsy structure. This is of particular concern during acute and emergency settings wherein patient and environmental factors require steadied instrumentation. Introducers of this length will wobble in free space above the patient, which transfers to the distal introducer (inside the patient). This can become a similarly haptic challenge at the proximal end when attempting to place and slide a endotracheal tube over the introducer.

TIS solves the unwieldiness of most introducers by sheathing them in material with relative stiffness (increased elasticity modulus through), including but not limited to PTFE with a specified ID/OD ratio (see below).

The invention will be more fully understood by reference to the following descriptions accompanying drawings.

FIELD OF THE INVENTION

Adjunct for airway intubation involving tracheal introducers.

BRIEF SUMMARY OF THE INVENTION

The present invention is an airway adjunct that allows for ease of passage of an introducer through the glottic opening. The placement of an introducer may be utilized to assist with the ultimate goal of endotracheal intubation, or for whatever the primary goal of the proceduralist, including, but not limited to placing an introducer primarily for emergent oxygenation through the introducer with central canula.

An unprecedented benefit of this invention is the ability to select an introducer on a clinical case-by-case basis (of varied size, style, shape and design) for sheathing into the TIS. An introducer sheathed in an TIS offers the proceduralist substantial improvement in haptic control, including improved maneuverability, remote distal articulating control, an improved force vector by sliding an introducer over a relatively stiff distal channel, and thus overall ease of use and safety profile.

This device supports manufacture of introducers by manufacturers who maintain particular knowledge and streamlined operations of introducers of varied material, specialty and function.

BRIEF DESCRIPTION OF THE SEVERAL VIEWS OF THE DRAWING(S)

DETAILED DESCRIPTION OF THE INVENTION

Figure 1:
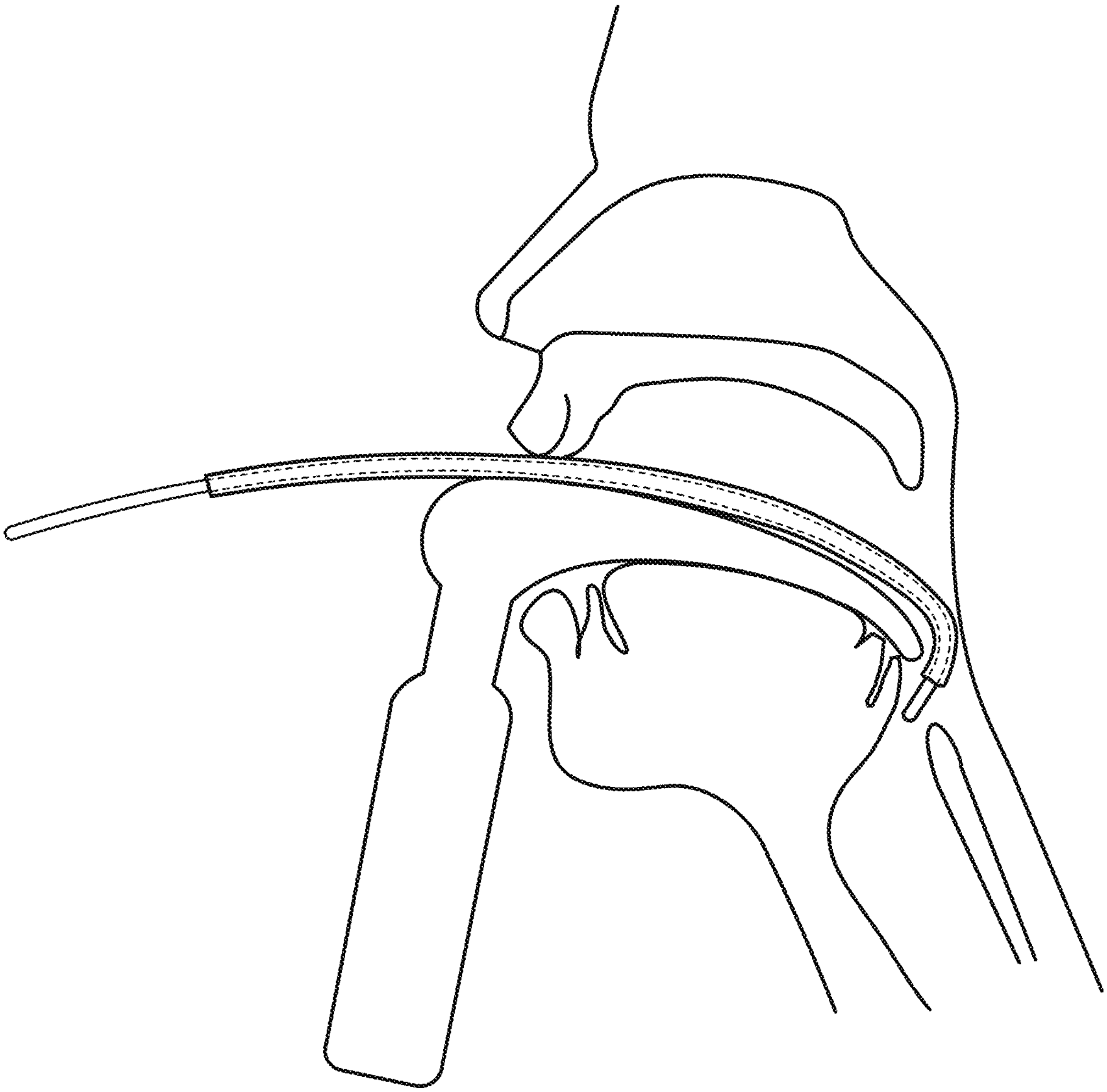
FIG. 1 is a schematic illustration of a human airway with a tracheal introducer sheath device with introducer placed within (also referred to as 'sheath-over-introducer assemblage').
Figure 2:
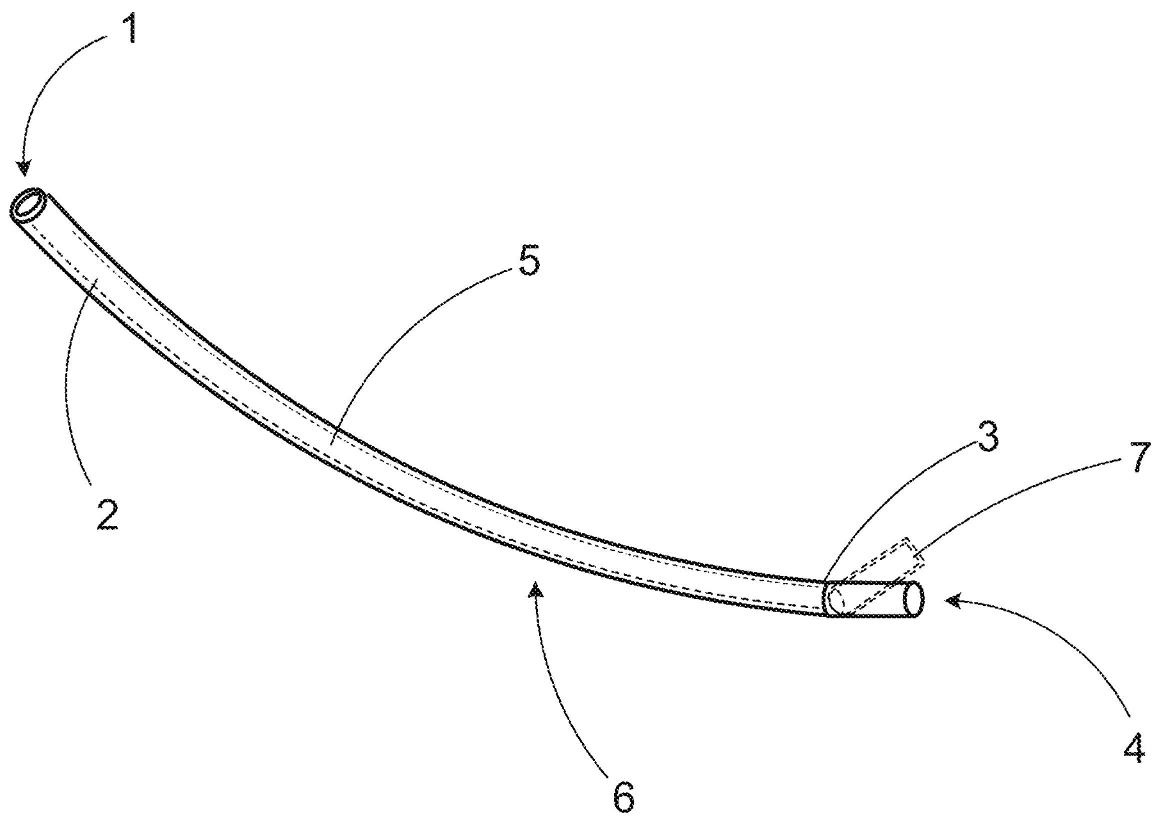
FIG. 2 shows the tracheal introducer sheath device.

FIG. 2 of the drawings illustrates a preferred embodiment of the invention which has been referred to hereinabove as a tracheal introducer sheath (TIS), since the instrument 6 is applicable to assisting passage of a tracheal introducer 10 into the airway, through the oropharynx 9 and past the glottis, for endotracheal intubation. It is to be understood, however, that instrument 6 is not limited to the aforementioned uses. It may, for example, be used for sheathing an introducer 10 of many types such as but not limited to one with a central lumen, for emergent airway oxygenation.

Instrument 6 comprises a main portion of the body 5, connecting an open-ended sheath (proximal opening 1 and distal opening 4) by a hollowed tube of PTFE, twelve to fifty centimeters long, with varied ID/OD ratios depending on the chosen length.

As a point of clarification, the length of each individual instrument 6 will generally not be modifiable. A notable functional exception would be if an introducer 10 manufacturer produced an introducer 10 with modifiable length. In this case, if the introducer 10 is placed through the instrument 6, length would be modifiable of the sheath-over-introducer assemblage.

For an adult instrument 6 of length between twelve and thirty centimeters long, the instrument 6 is to have an internal diameter (ID) ranging between 4 mm and 7 mm with outer diameter (OD) ranging between 6 mm and 9.5 mm. Tube thickness for an adult instrument 6 is to range from 0.5 to 3 mm. One embodiment for an adult size instrument 6 is 20.5 centimeters long with an ID of 6 mm and an OD of 8.4 mm, with a wall thickness of 1.2 mm.

For the same instrument 6 sized for children, the instrument 6 length is to range from between seven to fifteen centimeters long with IDs ranging between 2.5 mm and 5 mm. Outer diameters will range between 4.5 mm and 7 mm. Tube thickness for a pediatric version of instrument 6 is to range from 0.2 to 2 mm.

Figure 4:
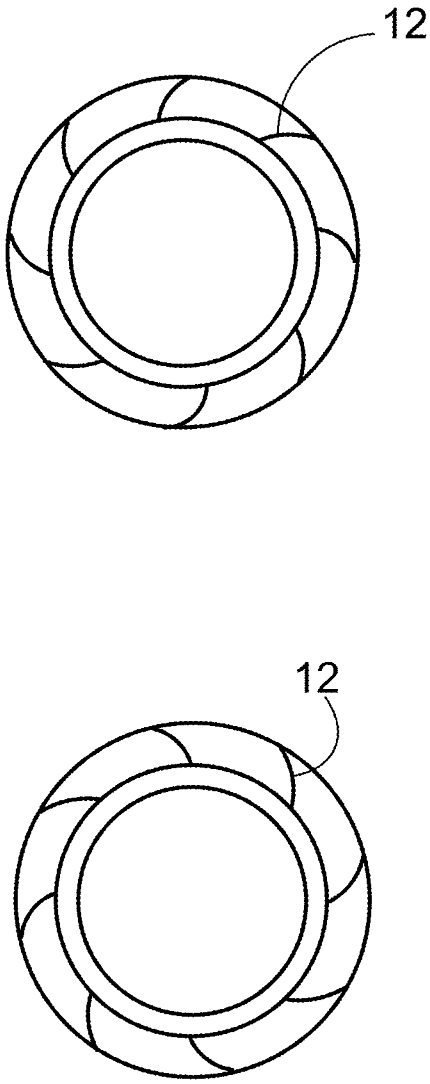
FIG. 4 illustrates an axial view of a TIS (but not a BTIS) from proximal and distal ends (above and below, respectively), showing vertebrated succession rigid annuli.

For the TIS but not the STIS, operator controlled articulation of the articulating component 3 occurs by applying a pull force to the proximal portion 2 of the instrument 6, which transmits along an internally installed vertebrate succession of rigid annuli 12 from the proximal portion 2 of the instrument 6 through the body 5 and into the articulating component 3 of the tip and distal opening 4, allowing for proximal operating wires (illustrated in FIG. 4) to effect a smoothly operating graduated bending over a substantial length of the instrument's 6 distal portion, without effect upon intermediate portion of the body 5 and proximal portions 2 of the sheath 6. The vertebrate succession of annuli 12 seen in FIG. 4 is installed internally to the smooth internal surface of the sheath, maintaining smooth passage of an introducer. For those interested in greater detail in the construction of a pull-sheath that maintains a uniformly diametrically dimensioned internal hollow cavity throughout a tube within which fiber bundles are extended, allowing simultaneous proximal-to-distal control of an articulating mechanism, see U.S. Pat. No. 3,913,568.

The articulating component 3 allows angulation 7 between five and ninety-five degrees.

The size of the internal diameter of the instrument is constant throughout each individual instrument 6 but can vary between different instruments 6, allowing for passage of different sized introducers 10 when desired by the proceduralist.

Figure 3:
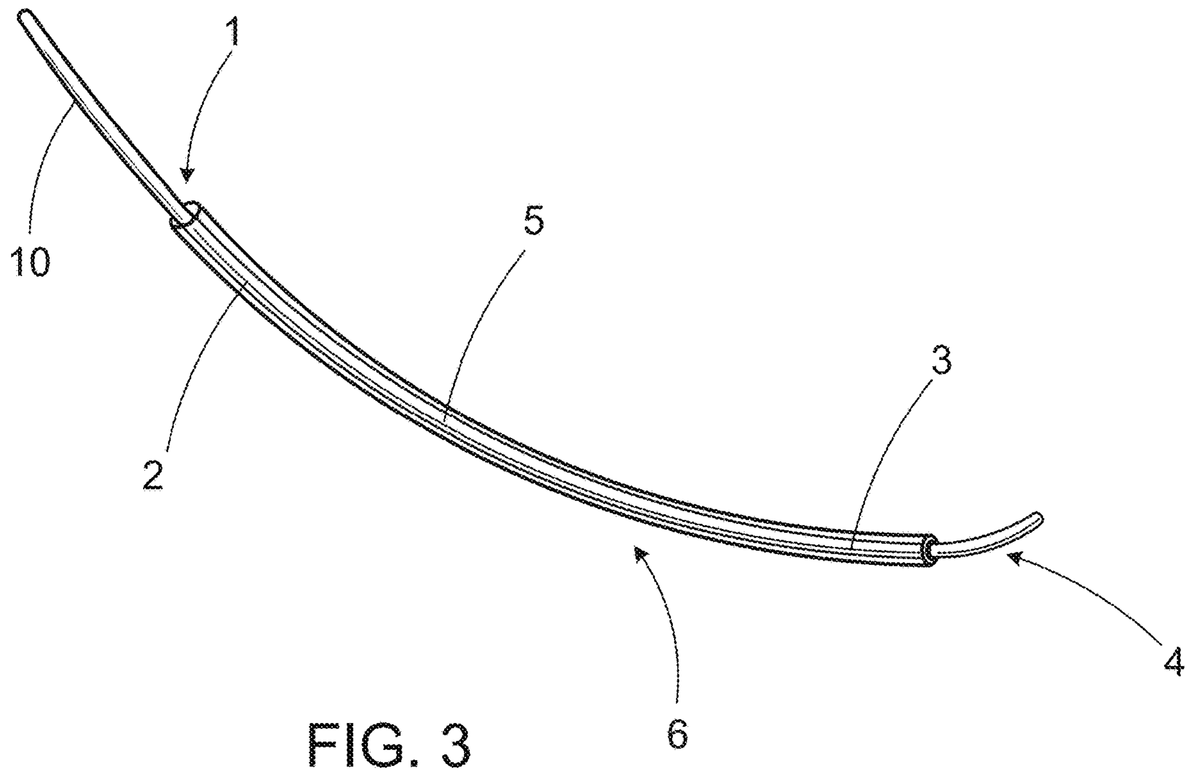
FIG. 3 illustrates an introducer device placed within the sheath of the tracheal introducer sheath.

FIG. 3 Illustrates a sheath-over-introducer assemblage, emphasizing both the adjunct nature of the instrument 6, to be utilized with an introducer 10, as well as the 360-degree free rotational movement of an introducer within an instrument 6.

Figure 5:
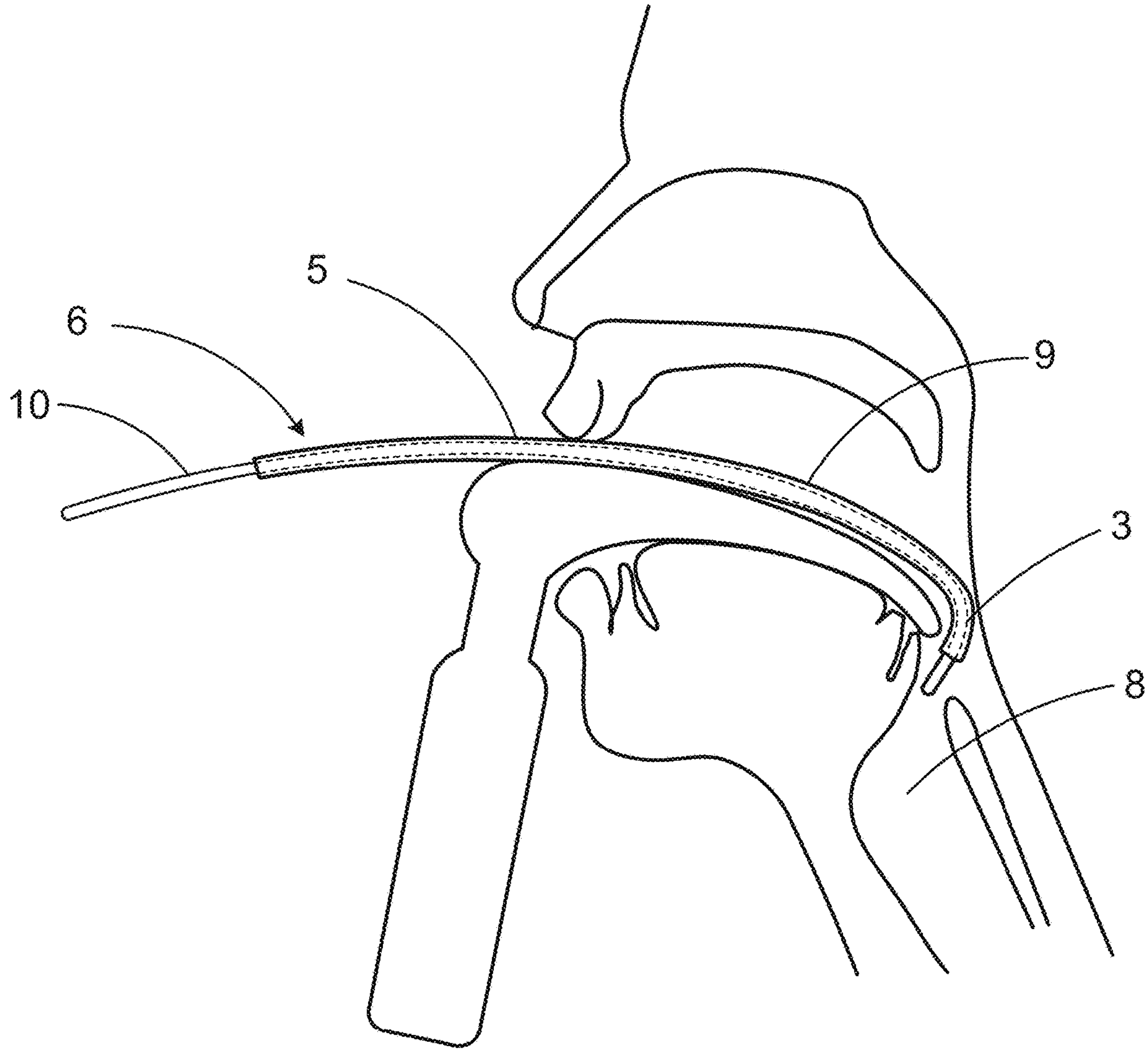
FIG. 5 is a schematic illustration of a human airway with laryngoscope assisted insertion of a sheath-over-introducer assemblage into the trachea.

The first steps of operating a tracheal sheath introducer 6 are illustrated in FIG. 5, during which a proceduralist uses either direct laryngoscopy or video-assisted laryngoscopy to insert a tracheal introducer sheath device 6 with introducer into the airway.

Figure 6:
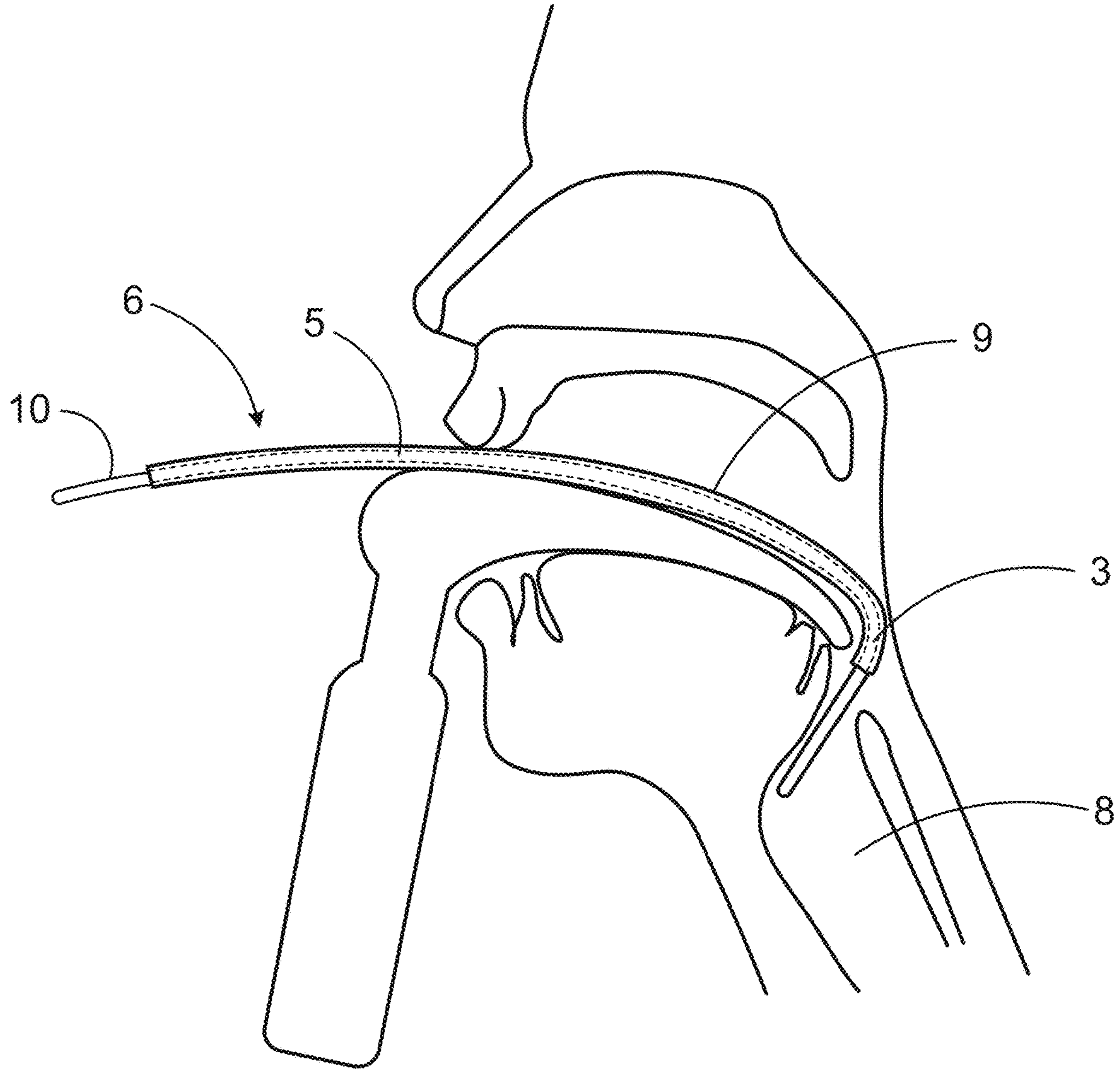
FIG. 6 is a schematic illustration of a human airway with laryngoscope assisted advancement of an introducer through the tracheal introducer sheath device until making contact with tracheal rings.

Once in appropriate proximity to the glottic opening, the tracheal introducer sheath device 6 is held in place, acting as a supporting vehicle through which the introducer is passed and directed towards the tracheal rings 8 (FIG. 6) until a vibratory sensation is felt that reflects tracheal ring 8 resistant forces have been met. Given the need to hold the laryngoscope and the sheath instrument 6, a third person trained in this procedure will advance the introducer 10 at the instruction of the main operator or proceduralist (holding the laryngoscope). Conversely, the proceduralist may ask an appropriately trained assistant to hold the sheath instrument 6 whilst the proceduralist advance the introducer 10.

Figure 7:
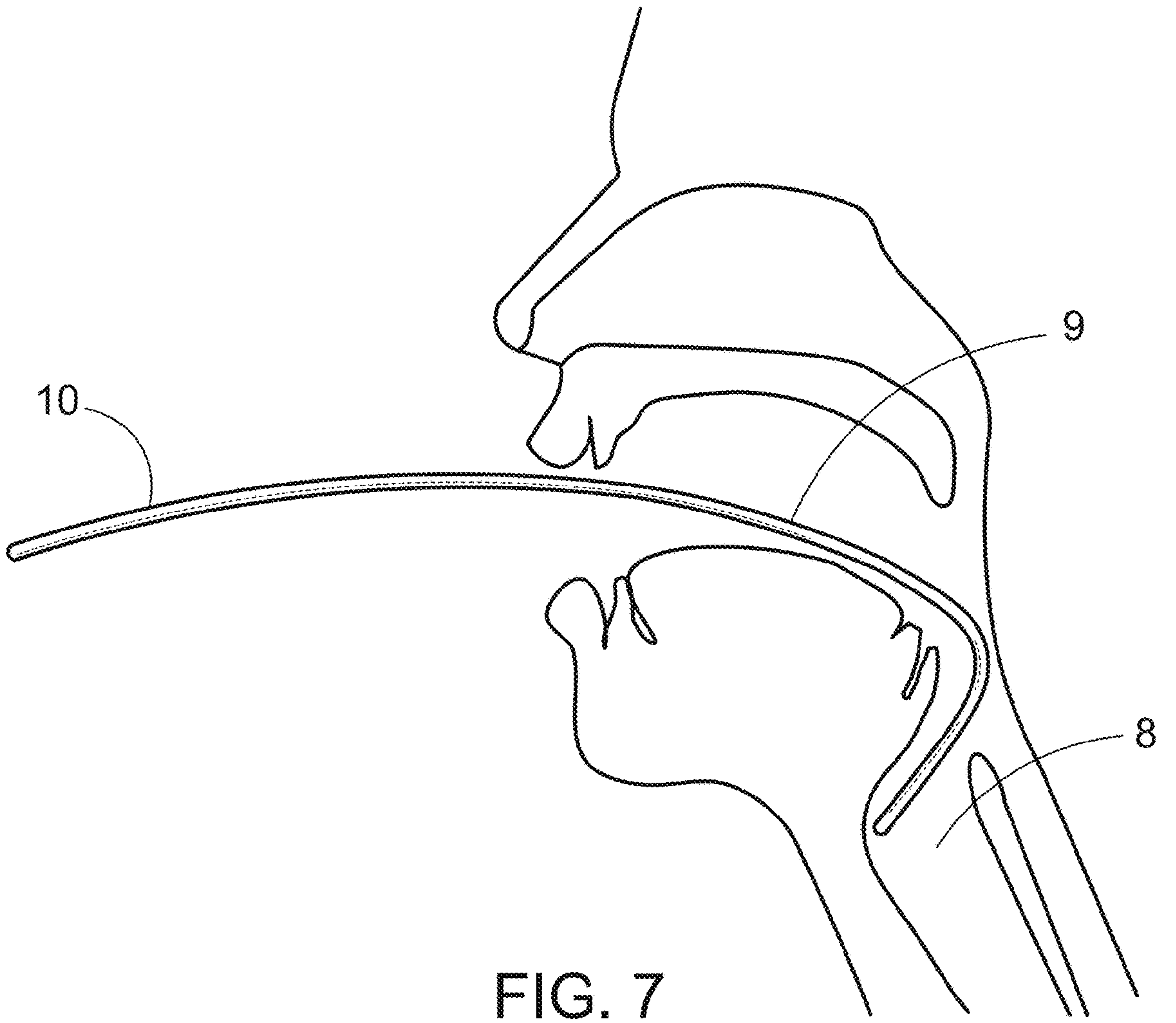
FIG. 7 is an illustration of a human airway with correct placement of an introducer in the trachea after a tracheal introducer sheath device has been removed.
Figure 8:
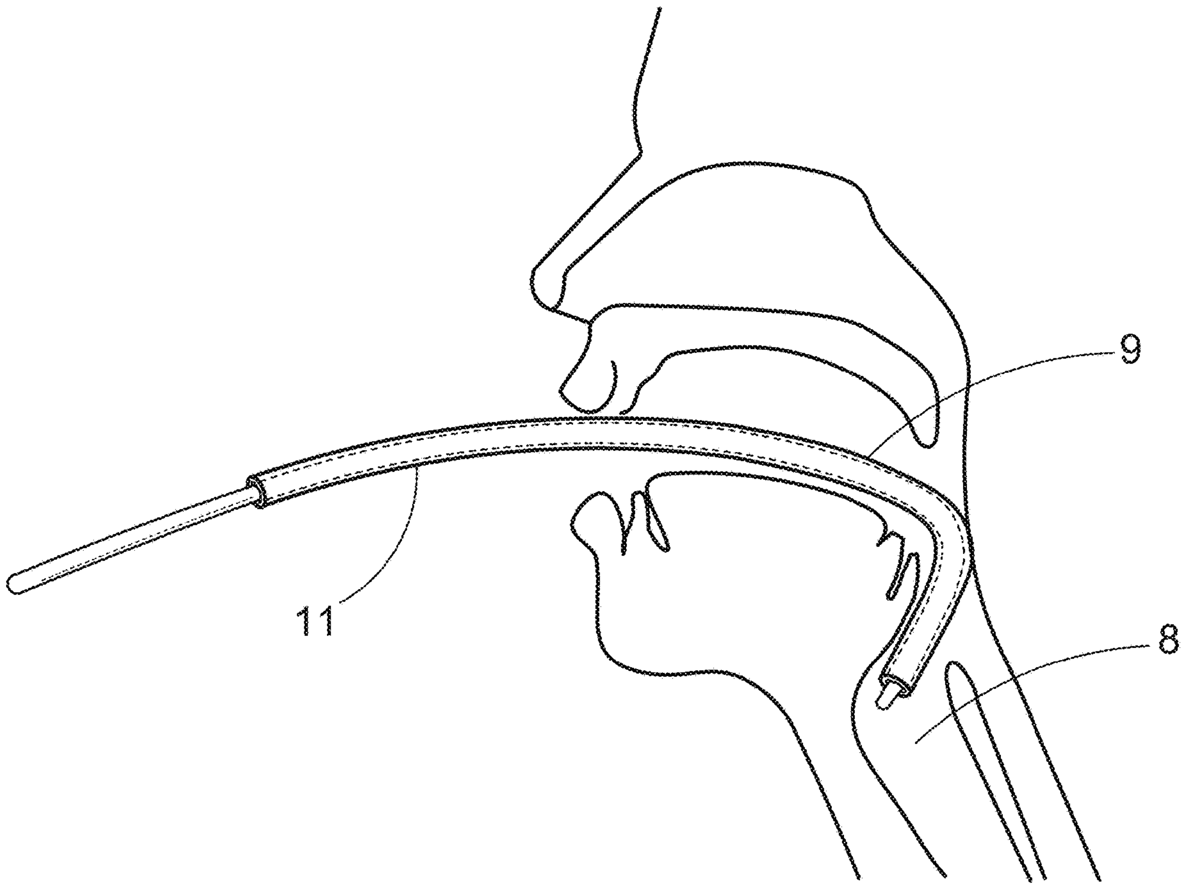
FIG. 8 is a schematic illustration of a human airway with correct placement of an endotracheal tube over an introducer and into the trachea.
Figure 9:
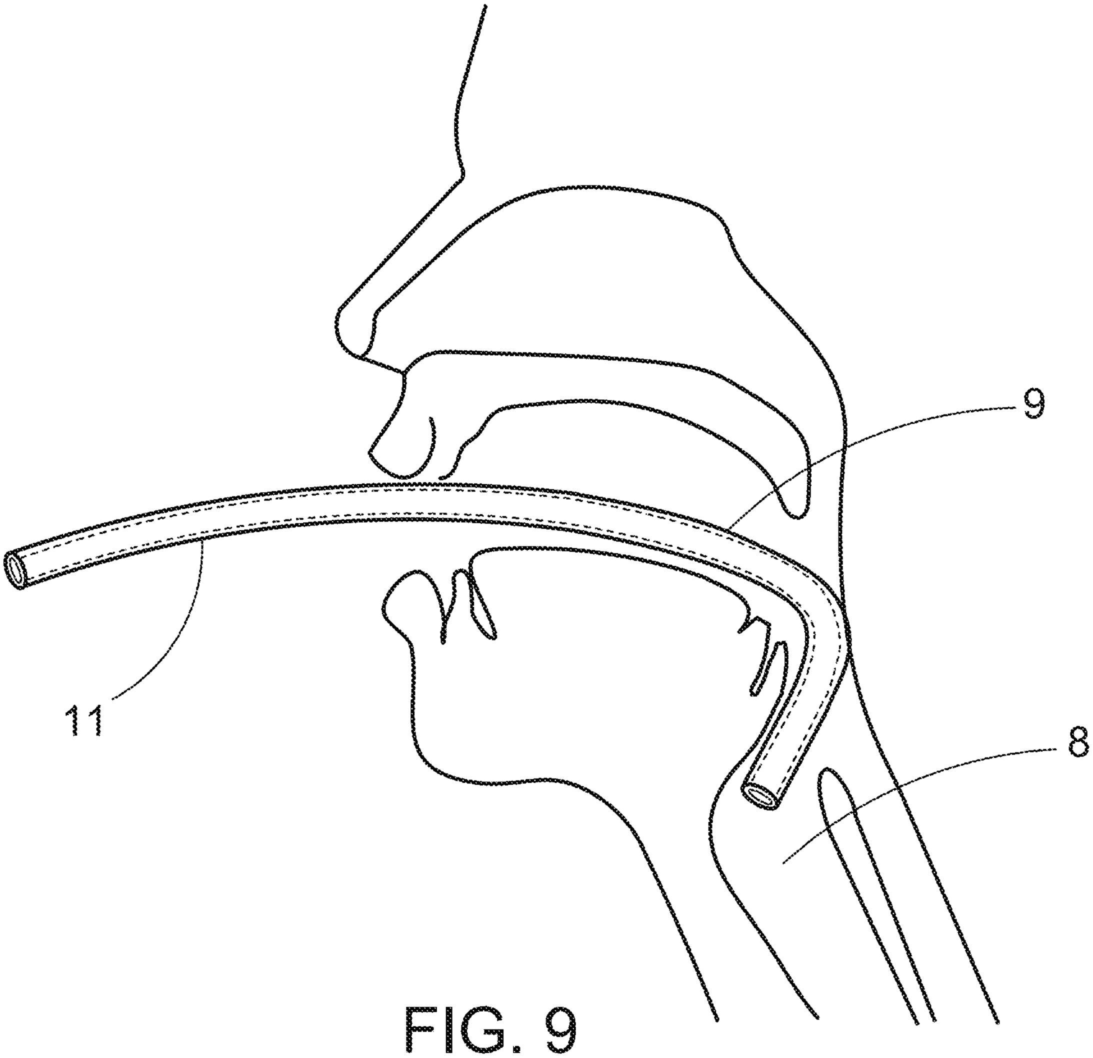
FIG. 9 illustrates the resulting position of the endotracheal tube after removal of an introducer.

At this point, the introducer 10 is held in place while the instrument 6 can be removed (FIG. 7) and an endotracheal tube 11 subsequently slid over the introducer 10 as in FIG. 8. The introducer is removed and endotracheal left in place (FIG. 9) for subsequent securing and mechanical ventilation.

The invention claimed is:

1. An assembly for assisting placement of an endotracheal tube into the airway of a person, comprising:

an elongated flexible tracheal introducer; and a tracheal introducer sheath shaped as a single component hollow tube that provides a sheath channel that extends from a proximal end of the sheath to a distal end of the sheath through which the tracheal introducer removably extends, wherein an inner diameter wall material of the tracheal introducer sheath configured to contact the elongated flexible tracheal introducer is relatively stiff in comparison with a stiffness of the tracheal introducer and which wherein the tracheal introducer sheath is manually moldable along its length to articulate different angles.

2. The assembly of claim 1, wherein the tracheal introducer sheath has a wall thickness of 0.2 mm to 2.0 mm.

3. The assembly of claim 1, wherein the tracheal introducer sheath's length is between twelve and fifty centimeters to provide coverage of the length of the tracheal introducer.

4. The assembly of claim 3, wherein the length of the tracheal introducer sheath is 20.5 cm.

5. The assembly of claim 1, wherein the tracheal introducer sheath comprises a vertebrate succession of rigid annuli from the proximal end of the sheath to the distal end of the tracheal introducer sheath.

6. The assembly of claim 1, wherein the tracheal introducer sheath includes operating wires along its length which provide means for gradually bending the tracheal introducer sheath through application of a pull force to a portion of the tracheal introducer sheath adjacent to the proximal end of the tracheal introducer sheath.

7. The assembly of claim 1, wherein a ratio of an outer diameter of the sheath and an inner diameter of the sheath is based on a chosen length of the sheath.

8. The assembly of claim 1, wherein a ratio of an outer diameter of the sheath and an inner diameter of the sheath is uniform along a chosen length of the sheath.

9. An assembly for assisting placement of an endotracheal tube into the airway of a person, comprising:

an elongated flexible tracheal introducer; and a tracheal introducer sheath shaped as a single component hollow tube that provides a sheath channel that extends from a proximal end of the sheath to a distal end of the sheath through which the tracheal introducer removably extends, wherein an inner diameter wall material of the tracheal introducer sheath configured to contact the elongated flexible tracheal introducer is relatively stiff in comparison with a stiffness of the tracheal introducer and wherein the tracheal introducer sheath is manually moldable along its length to articulate different angles;

wherein the tracheal introducer sheath has a wall thickness of 0.2 mm to 3.0 mm; and wherein the tracheal introducer sheath includes operating wires along its length, wherein the operating wires are configured to gradually bend the tracheal introducer sheath in response to application of a pull force to a portion adjacent to the proximal end of the tracheal introducer sheath.

10. The assembly of claim 9, wherein the tracheal introducer sheath's length is between 12-50 cm.

11. The assembly of claim 10, wherein the tracheal introducer sheath's length is 20.5 cm.

12. The assembly of claim 11, wherein the tracheal introducer sheath comprises a vertebrate succession of rigid annuli that extend from the proximal end of the tracheal introducer sheath to the distal end of the tracheal introducer sheath.

13. The assembly of claim 9, wherein a ratio of an outer diameter of the sheath and an inner diameter of the sheath is based on a chosen length of the sheath.

14. The assembly of claim 9, wherein a ratio of an outer diameter of the sheath and an inner diameter of the sheath is uniform along a chosen length of the sheath.

15. A method for guiding insertion of a tracheal introducer for subsequent placement of an endotracheal tube into the airway of a person, the method comprising:

providing a tracheal introducer sheath shaped in a single component hollow tube that defines a sheath channel from a proximal end of the sheath to a distal end end of the sheath through which the tracheal introducer removably extends, wherein an inner diameter wall material of the tracheal introducer sheath configured to contact the tracheal introducer is relatively stiff in comparison with a stiffness of the tracheal introducer and wherein the tracheal introducer sheath is manually moldable along its length to articulate different angles;

bending the tracheal introducer sheath into a shape for desired placement of the distal end of the sheath within the airway;

inserting the tracheal introducer sheath into the airway;

guiding the tracheal introducer into a glottic opening of the person's airway via the tracheal introducer sheath;

removing the tracheal introducer sheath from the tracheal introducer when a distal end of the tracheal introducer is determined to be properly placed within the airway;

positioning an endotracheal tube over the tracheal introducer; and removing the tracheal introducer from the airway after positioning the endotracheal tube.

16. The method of claim 15, wherein the tracheal introducer sheath has a wall thickness of 0.2 mm to 2.0 mm.

17. The method of claim 15, wherein the tracheal introducer sheath's length is between twelve and fifty centimeters to provide coverage of the length of the tracheal introducer.

18. The method of claim 17, wherein the tracheal introducer sheath's length is 20.5 cm.

19. The method of claim 15, wherein the tracheal introducer sheath comprises a vertebrate succession of rigid annuli from the proximal end of the tracheal introducer sheath to the distal end of the tracheal introducer sheath.

20. The method of claim 19, including the step of applying a pull force to a portion of the tracheal introducer sheath adjacent to the proximal end of the tracheal introducer sheath, to affect a gradual bending along the length of the tracheal introducer sheath.

21. The method of claim 15, wherein a ratio of an outer diameter of the sheath and an inner diameter of the sheath is based on a chosen length of the sheath.

22. The method of claim 15, wherein a ratio of an outer diameter of the sheath and an inner diameter of the sheath is uniform along a chosen length of the sheath.

23. A method for guiding insertion of a tracheal introducer through a tracheal introducer sheath for subsequent placement of an endotracheal tube into the airway of a person, the method comprising:

inserting the tracheal introducer sheath into the airway, the tracheal introducer sheath shaped as a single component hollow tube comprises an inner wall diameter material configured to contact the tracheal introducer, the inner wall diameter material is relatively stiff in comparison with a stiffness of the tracheal introducer, and wherein the sheath provides a sheath channel from a proximal end of the sheath to a distal end of the sheath, wherein the distal end portion of the tracheal introducer sheath comprises an articulating component which is manually moldable to articulate different angles through manual manipulation of the proximal end of the tracheal introducer sheath;

guiding the tracheal introducer into a glottic opening of a person's airway via the tracheal introducer sheath;

applying a pull force to a portion of the tracheal introducer sheath adjacent to the proximal end to iteratively control a gradual bending of the articulating component relative to an adjacent portion of the tracheal introducer sheath to position a distal end of the tracheal introducer within the airway, wherein the pull force controls proximal operating wires which gradually bend the articulating component relative to an adjacent portion of the tracheal introducer sheath;

determining whether the tracheal introducer is properly placed within the airway based on vibratory feedback to the proximal ends of the tracheal introducer and/or the tracheal introducer sheath;

removing the tracheal introducer sheath from the tracheal introducer when the distal end of the tracheal introducer is determined to be properly placed within the airway;

positioning an endotracheal tube over the tracheal introducer; and removing the tracheal introducer from the airway after positioning the endotracheal tube.

24. The method of claim 23, wherein the tracheal introducer sheath comprises a vertebrate succession of rigid annuli from the proximal end to the articulating component.

25. The method of claim 24, wherein applying the pull force to a portion of the tracheal introducer sheath adjacent to the proximal end, controls through the vertebrate succession of rigid annuli the gradual bending of the articulating component.

26. The method according to claim 23, wherein the tracheal introducer sheath has a wall thickness of 0.2 mm to 3.0 mm.

27. The method of claim 23, wherein a ratio of an outer diameter of the sheath and an inner diameter of the sheath is based on a chosen length of the sheath.

28. The method of claim 23, wherein a ratio of an outer diameter of the sheath and an inner diameter of the sheath is uniform along a chosen length of the sheath.

* * * * *